United States Patent [19]
Allgeyer

[11] Patent Number: 5,730,758
[45] Date of Patent: Mar. 24, 1998

[54] STAPLE AND STAPLE APPLICATOR FOR USE IN SKIN FIXATION OF CATHETERS

[76] Inventor: Dean O. Allgeyer, 762 Glenmont Ave., Los Angeles, Calif. 90024

[21] Appl. No.: 710,167

[22] Filed: Sep. 12, 1996

[51] Int. Cl.$^6$ .................................................. A61B 17/04
[52] U.S. Cl. ................................................................ 606/219
[58] Field of Search ............................. 606/219; 227/19, 227/175.1–180

[56] References Cited

U.S. PATENT DOCUMENTS

4,434,796  3/1984  Karapetian ........................ 606/219

*Primary Examiner*—Gary Jackson
*Attorney, Agent, or Firm*—Samuel L. Alberstadt

[57] ABSTRACT

An inexpensive surgical stapler, such as for use in securing vascular catheters, has a plastic applicator made for use with a single staple. The applicator has a backbone and two identical arms. The inside face of the backbone has a retaining channel that secures the crown portion of the staple against movement. The inside faces of the arms have guidance grooves that direct the movement of the staple as the applicator arms are squeezed with finger pressure. The outside faces of the arms are configured to permit gripping by the operator's fingers. The stapler can be used in lieu of suturing. Other staple and applicator assemblies can include two or more such assemblies.

19 Claims, 13 Drawing Sheets

STAPLE AND STAPLE APPLICATOR FOR USE IN SKIN FIXATION OF CATHETERS

BACKGROUND OF THE INVENTION

This invention relates to medical staples and stapling devices. More particularly, the invention relates to a staple in combination with a flexible, digitally manipulable, anvilless staple applicator that is useful for affixing catheters to the skin and for other medical procedures.

Medical stapling devices have been routinely in use for some time. They are designed chiefly to replace the suturing process because of the significantly less time used in stapling. A variety of devices are known. For example, Green, U.S. Pat. No. 5,158,567, describes an anvilless surgical stapler with articulated handles and a slidable staple cartridge mounted in a block at the distal end of the handles. Samuels, U.S. Pat. No. 4,399,810, describes a skin clip applied with an articulating device containing a substantial number of staples. The staples are closed by a lateral pressure from the articulating applier. U.S. Pat. Nos. 4,719,917 and 4,526,174 disclose other medical staples.

In surgical and anesthetic practice, it is common to place indwelling catheters for vascular access. These catheters require fixation to the skin to maintain their position, thus avoiding potential injury to the patient or withdrawal of the catheter. Currently, fixation to the skin is accomplished by suturing the catheter hub to the underlying skin. A needle and suture are passed through the skin and hub eye, or eyes, and tied into a knot.

This procedure includes an attendant risk of needle stick. To avoid that risk would require the use of a stapler kit, which is far too costly to justify its use for one or two staples. The use of a stapler would save considerable time over suturing, especially when considering the daily frequency of catheter fixations in clinical situations, but the cost of a stapler kit is orders of magnitude greater than that for a suturing kit.

SUMMARY OF THE INVENTION

The present invention allows fixation of catheters to the skin in a less time-consuming and safer manner than either suturing or the use of traditional medical staplers. The cost of the materials is anticipated to be, for practical purposes, approximately the equivalent of suturing.

The present invention is a method of stapling and a device for performing that method. The device comprises an applicator assembly, preferably made of sterilizable, medical grade plastic, and is disposable. A staple is fabricated from stainless steel or other commonly used FDA approved staple material, and is inserted into the applicator to form the assembly. The applicator has no anvil and is both flexible and digitally manipulable.

The staple includes a crown portion with legs obliquely positioned at the ends of the crown. The legs terminate in points capable of piercing the skin. In the preferred embodiment of the invention, a single staple is mounted in the applicator.

The applicator is shaped generally like an inverted "U," with an open bottom to permit the exiting of a closed staple attached to the skin. The inner faces of the applicator include a stabilizing channel and grooves that retain the staple during both storage and application, and guide it during the application process. The outside faces of the two opposing arms of the applicator are preferably a relatively non-slip surface to facilitate a digital grasp of the applicator and to permit digital deformation of the applicator, which in turn deforms the staple.

In its preferred use, an applicator with staple is positioned to cause one of the two staple legs to traverse the catheter hub eye and both staple legs to pierce the skin when lateral forces are manually applied to the applicator arms. Closure of the staple then results in fixation of the catheter to the skin. The applicator can subsequently be slid off the staple, which is no longer held by the applicator due to the change in staple configuration relative to the released applicator.

In an alternate embodiment, two or more applicator and staple combinations are joined together to provide a device that can be used when two or more staples are necessary.

Accordingly, there are several objects and advantages to my invention. One advantage provides a means for securing a catheter to the skin using a surgical staple and applicator in a less time-consuming procedure than suturing.

Another advantage permits securing the catheter to the skin with less risk of needle stick injury when compared to the traditional method of suturing.

An object of the invention is to provide a stapler for affixing a catheter to the skin that is, relative to other staplers, less expensive to manufacture, easy to distribute and store in a clinical environment, and is both simple and reliable to use.

Still another object of the invention is to provide the availability of a small number of staples when the use of a traditional stapler kit is not economical.

These and other objects and advantages will become apparent in conjunction with the detailed description and the following drawings.

DETAILED DESCRIPTION OF THE PREFERRED EMBODIMENTS

Figure 1:
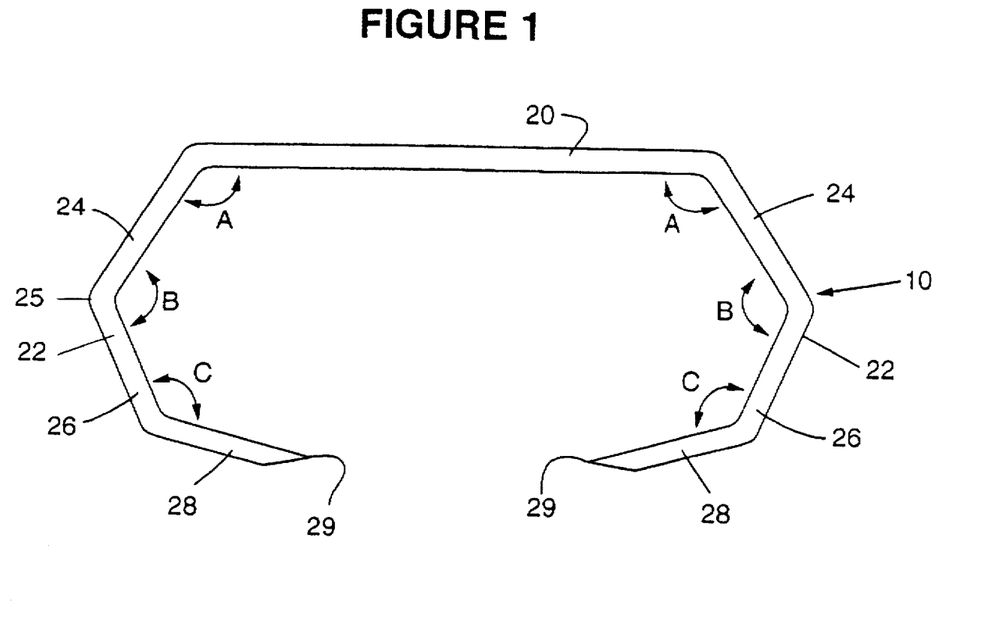
FIG. 1 shows a surgical staple in the open position.

Referring now to FIG. 1, a staple 10 is constructed of stainless steel, titanium, or other similarly deformable material which retains the shape to which it has been deformed. The staple 10 includes a crown portion 20 and opposingly disposed legs 22. In the preferred embodiment, the crown 20 is generally horizontal and connected to legs 22 at each end. Legs 22 are preferably identical and comprised of three segments, 24, 26, and 28, terminating in skin piercing point 29. The three leg segments 24, 26, 28 are offset by three oblique angles A, B, and C, which are approximately 120 degrees each.

Figure 2:
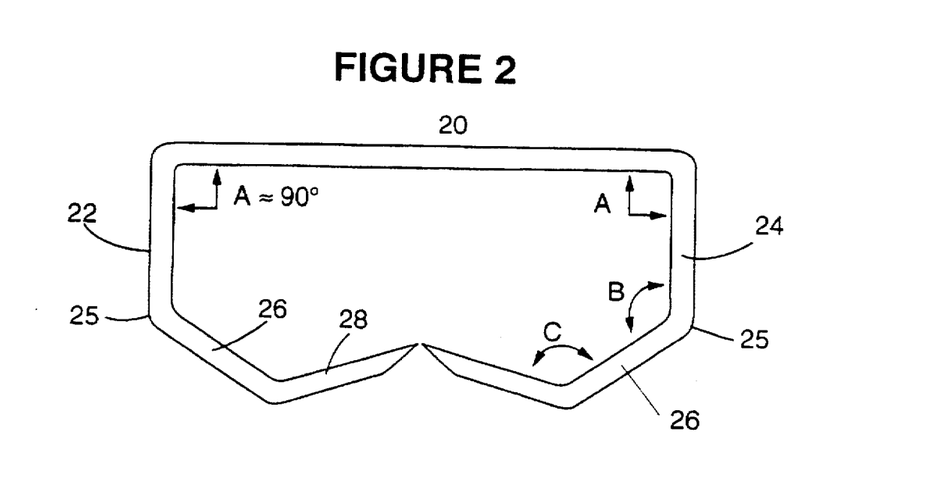
FIG. 2 shows the staple in the closed position.

FIG. 2 depicts the staple in its closed, deformed configuration. After the staple has been completely closed and the applicator withdrawn, angle A between crown 20 and leg segment 24 should be approximately a 90 degree right angle.

Figure 3:
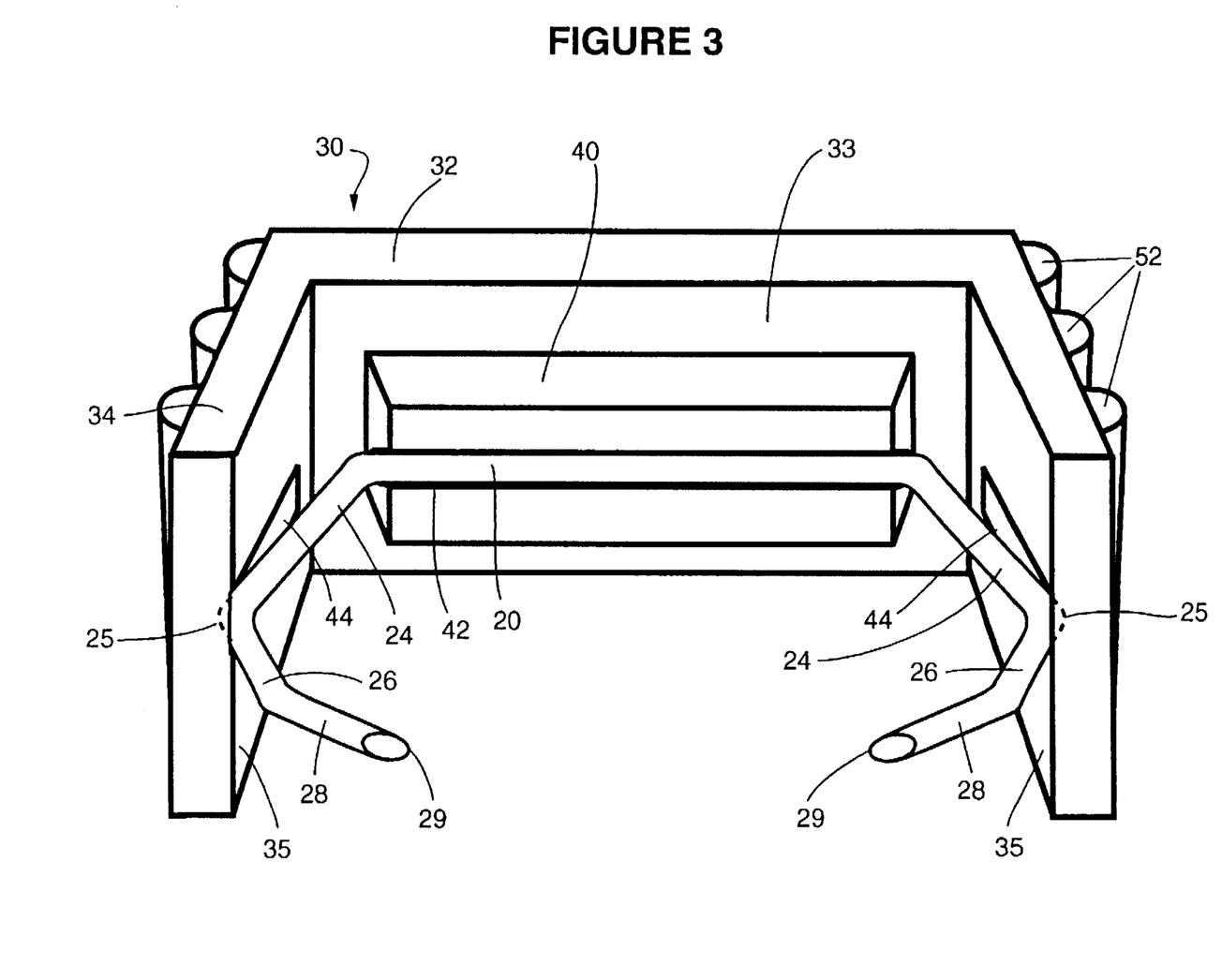
FIG. 3 is a perspective view of a staple applicator and staple.
Figure 4:
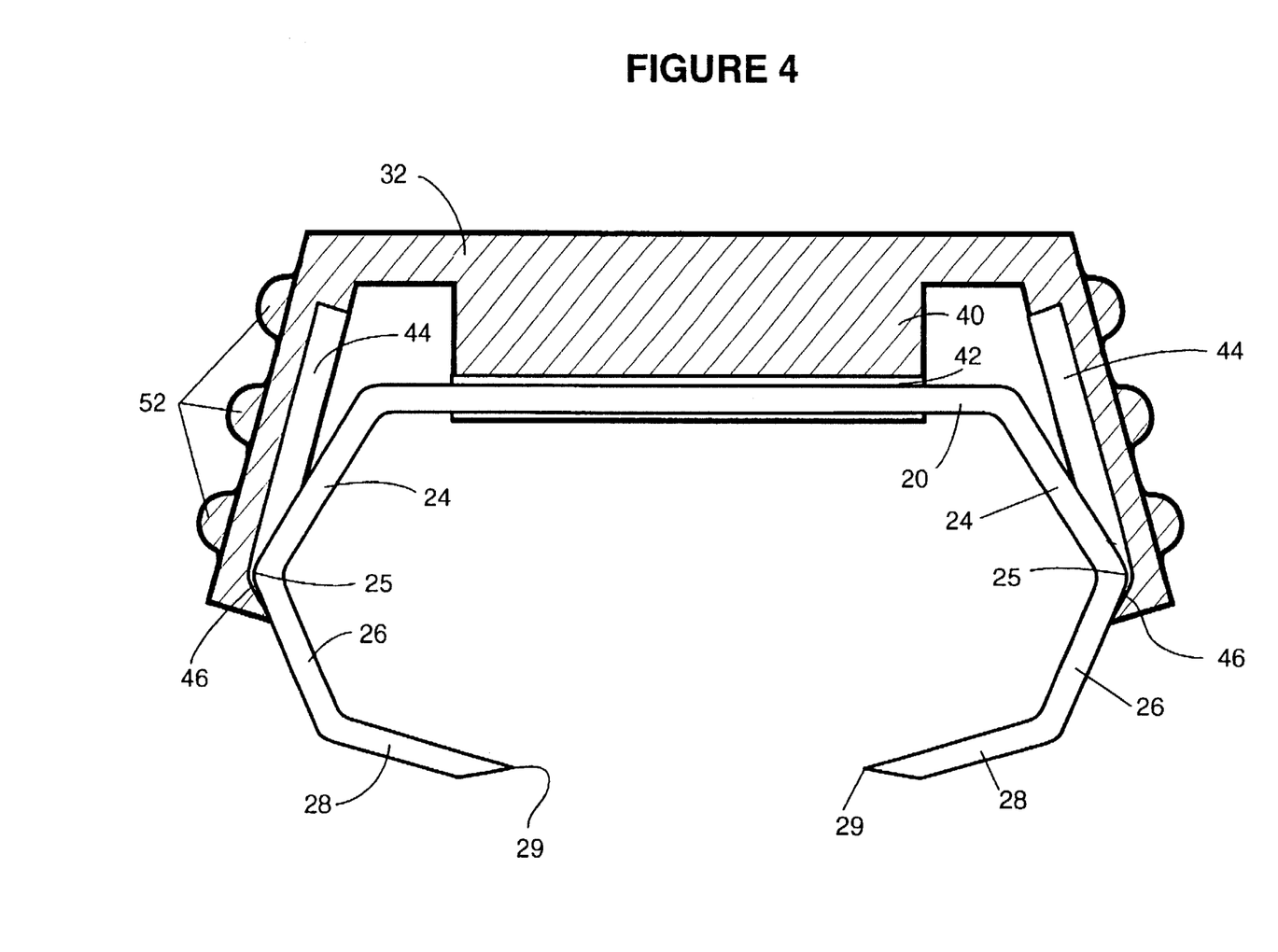
FIG. 4 is a cross section of one embodiment of the applicator and staple.
Figure 5:
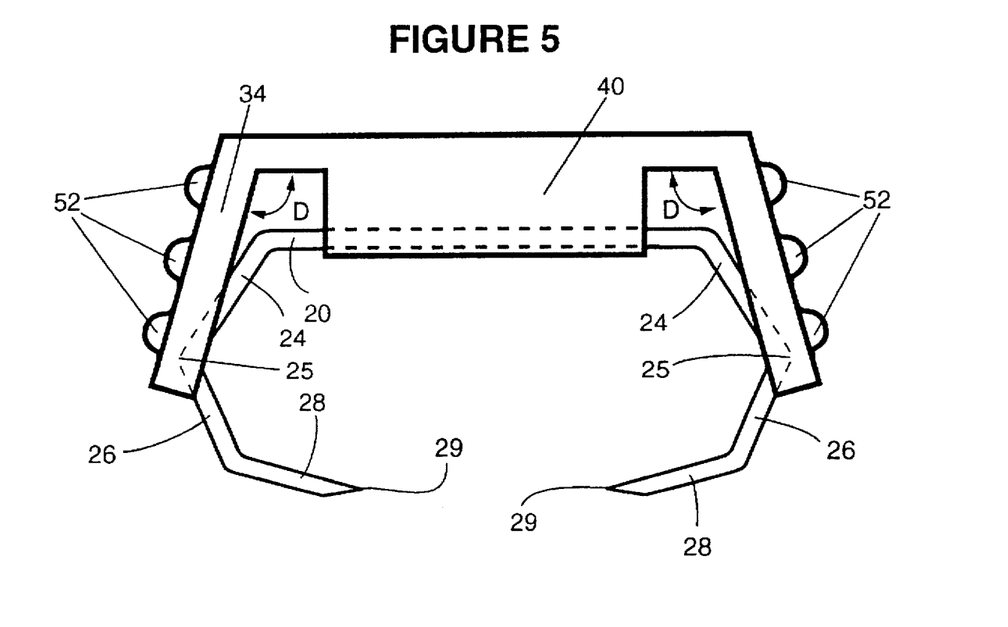
FIG. 5 is an elevation view of the applicator with the staple in the open position.

FIGS. 3, 4, and 5 depict an anvilless applicator 30 holding a staple 10 in the open position. The applicator comprises a top or backbone portion 32 and two arms 34. The inside face 33 of backbone 32 includes a stabilizing block 40 with stabilizing channel 42 that prevents the staple from rotating about point 25 between leg segments 24 and 26.

The inside faces 35 of the applicator arms 34 contain guidance and retaining grooves 44 into which staple leg points 25 are slidably and releasably mounted. Grooves 44 terminate in a curved portion 46, so that contact between the staple and the applicator is maintained while the staple is compressed during application. The staple should be mounted and retained in the applicator with a slight degree of snugness, so the staple does not fall out prior to use. At the same time, the staple should be easily releasable from grooves 44 and channel 42 once the staple has been applied. The outside face of the applicator arms 34 includes a means for digitally holding and compressing the applicator arms 34. In the present invention, that means is preferably a series of ribs 52 on each applicator arm 34. Other cupped, polygonal, non-uniform, or rough surfaces are equivalent to the ribs, as those of skill in the art will appreciate.

It should be noted that the present invention comprises a Class I medical device, e.g., a skin stapler with removable staples and nonabsorbent legs. Under FDA regulations, a Class I medical device does not require pre-notification of, or approval from, the FDA. Thus, this invention can be practiced with little or no regulatory costs or delays.

Figure 7:
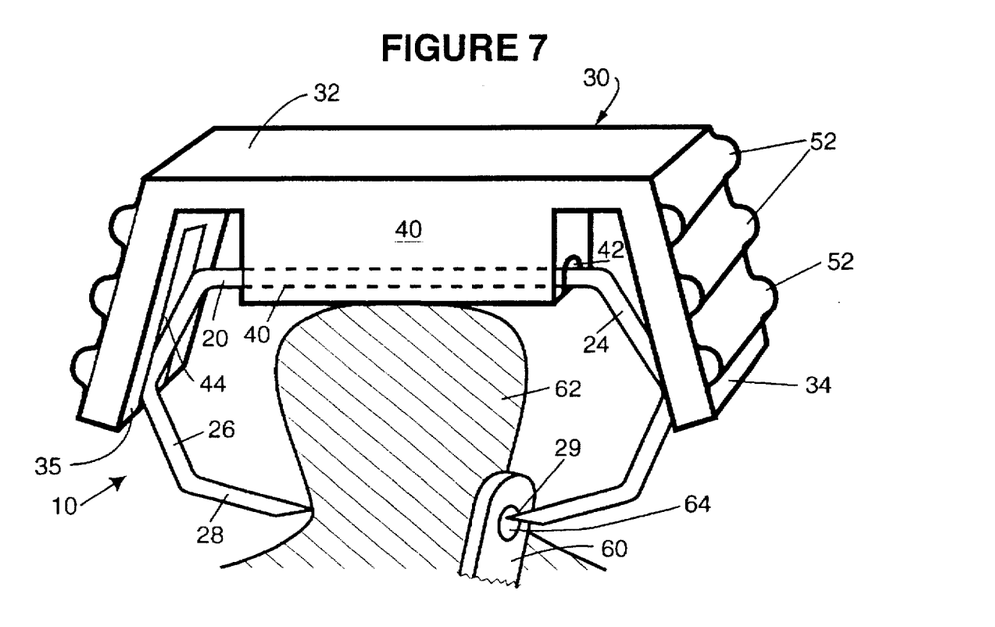
FIG. 7 is a perspective view of the applicator and staple adjacent to, and prior to the clamping of, the skin and hub eye.

Prior to using the present invention, a transcutaneous vascular catheter is placed in the patient in the usual manner (not shown). Referring now to the additional figures, the applicator 30 containing a staple 10 is held between the thumb and second finger of the operator's dominant hand. The open staple points 29 are held away from the operator. The operator's other hand is used to manipulate the catheter hub 60 and underlying skin 62, so the skin 62 is tented (see FIG. 7) and positioned to receive staple 10. The applicator and staple assembly is positioned so one staple piercing point 29 traverses the eye 64 of catheter hub 60 and both points 29 come to rest on the base of the tented skin. The tented skin 62 has been manipulated to rest between the open staple legs 22 through a combination of tenting by the non-dominant hand and positioning of the applicator 30 and staple 10 by the dominant hand.

Figure 6:
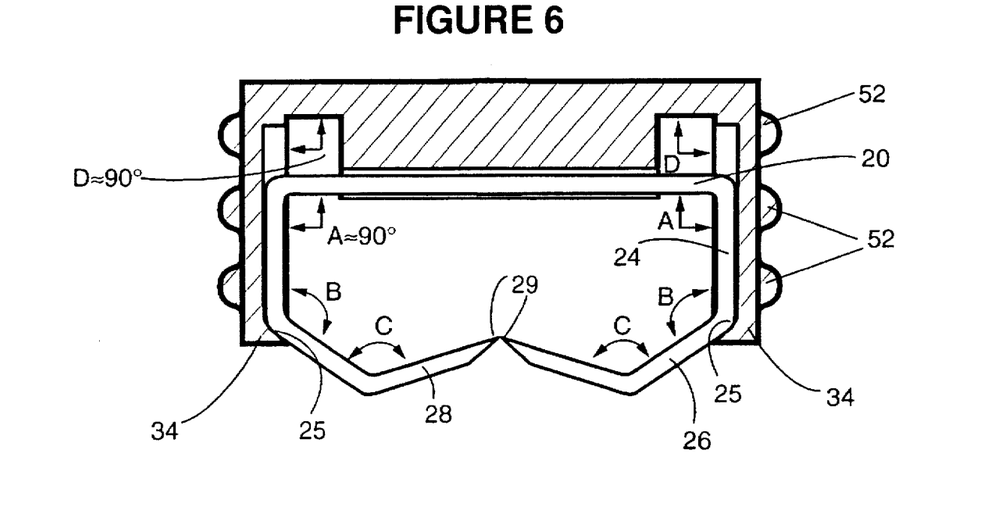
FIG. 6 is an elevation view of the applicator containing the staple in the closed position.
Figure 8:
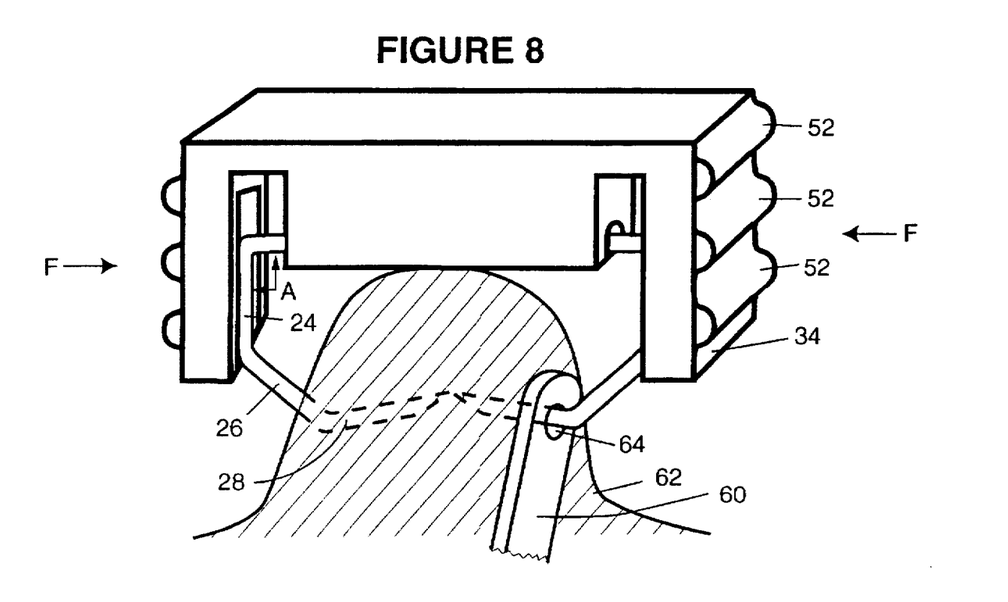
FIG. 8 is a perspective view of the applicator and staple after clamping the skin and hub eye.
Figure 9:
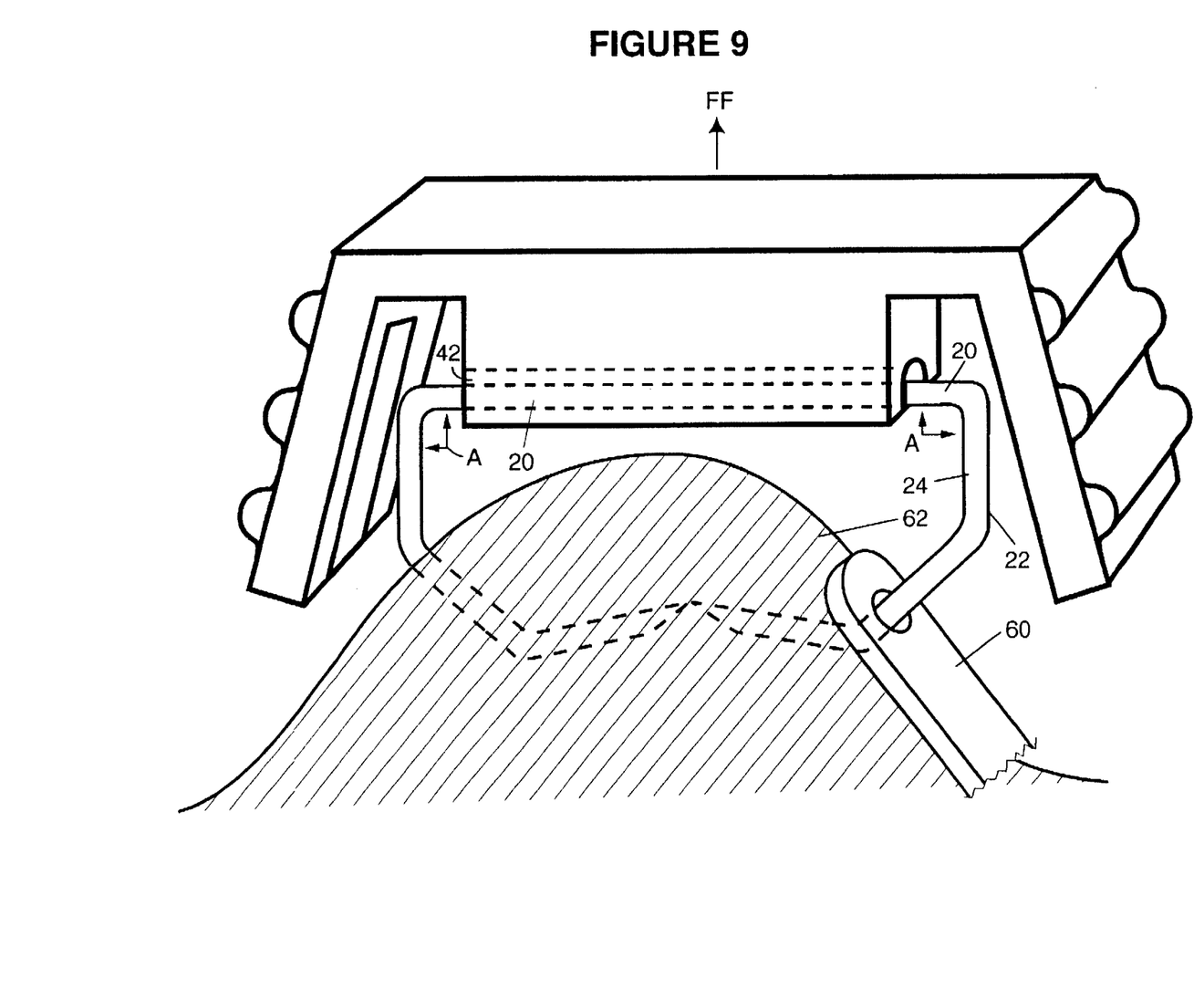
FIG. 9 is an elevation view of the applied staple after the legs of the applicator have been released.

The staple is closed by squeezing the applicator arms 34 with one's fingers, which generates a closing force F (see FIG. 8). This causes the piercing points 29 to penetrate the skin. The medial progress of the applicator arms 34 is arrested by the ends of crown 20 at approximately a ninety degree angle D (see FIGS. 5 and 6). After the applicator arms 34 are released (see FIG. 9), there is a small, almost imperceptible, spring-like rebound of the staple legs 22. For practical purposes, the angle between the staple crown 20 and legs 22 remains approximately 90 degrees.

A staple used in the described embodiment must have at least two leg segments that form an angle whose intersecting point is outside the ends of crown portion 20. Such a configuration would be analogous to leg segments 24,26 meeting at point 25, which is outside the end of staple crown 20—a necessary configuration so that the applicator arms 34 can provide a lateral force to secure the staple to the skin. While the preferred embodiment contemplates a staple like that shown in FIG. 1, it is possible to employ other, differently shaped staples that come within the scope of the patent. Indeed, the applicator and staple could be configured so that the applicator backbone and arms would begin the application with angle D at approximately 90 degrees.

When the squeezed applicator arms 34 are released, applicator arms 34 generally regain their original configuration in relation to applicator backbone 32. Applicator 30 can then be removed from staple 10, because staple 10 is no longer held by grooves 44. In the preferred embodiment, it is contemplated that grooves 44 frictionally hold staple 10 prior to use, although only a small force is required to release staple 10 from grooves 44. Here that force would simply consist of the rebound of plastic applicator arms 34. Also in the preferred embodiment, stabilizing channel 42 is large enough so that staple crown 20 can be loosely contained in the space of channel 42. Thus, in FIG. 9 the upward force FF required to lift the applicator 30 off staple 10 after use is simply the force required to overcome the weight of the applicator 30.

Figure 10:
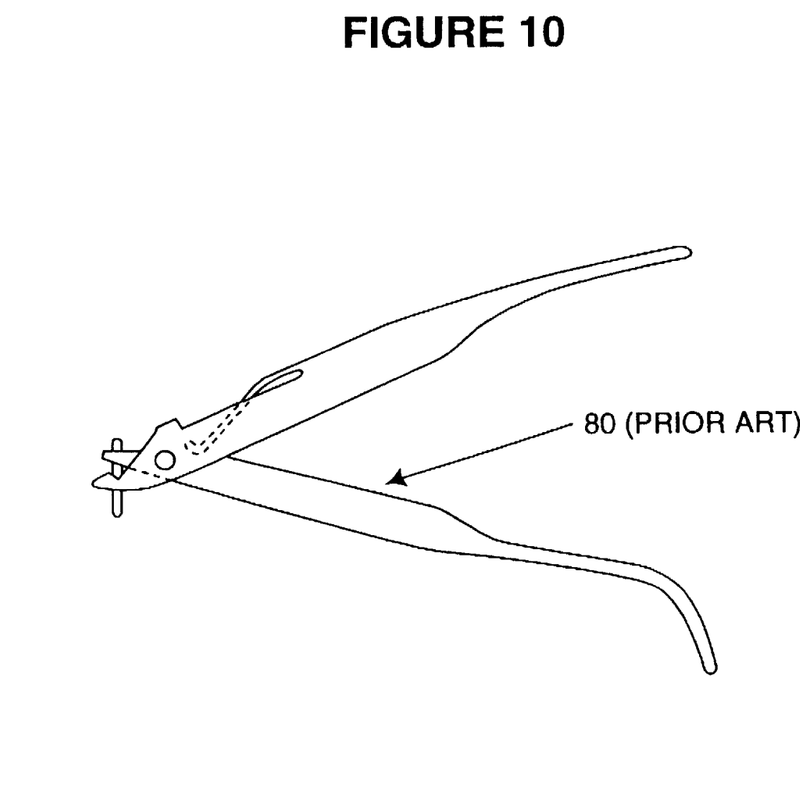
FIG. 10 depicts a standard staple remover, which is part of the prior art.
Figure 11:
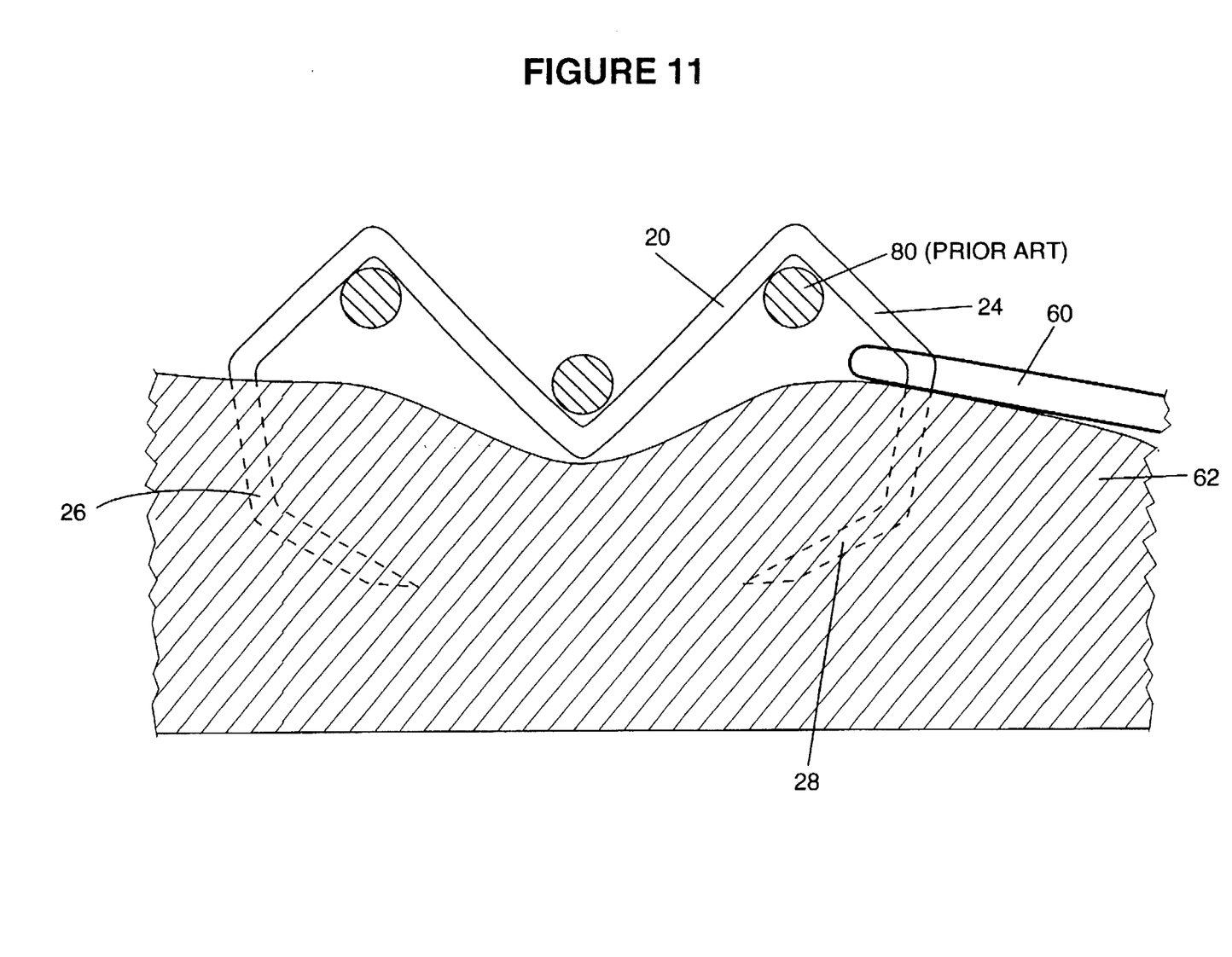
FIG. 11 is a cross section of a staple being removed.

Once the staple is applied, the applicator can be discarded. When the staple must be removed from the patient, it can be accomplished in a traditional, prior art manner (see FIGS. 10-11) and a dressing applied as necessary.

For a catheter hub with two eyes, one can approach the problem in at least two different ways. First, one can use two separate assemblies of a single applicator and staple. Alternatively, one can use a second embodiment of the invention, a dual applicator 100 (FIG. 12) that is made from two separate assemblies 100A, 100B, with each assembly made of a single staple 110 and single applicator 130. The assemblies are preferably connected by a plastic bridge or joining member 120. The second staple can be applied by rotating the applicator one hundred eighty degrees with the dominant hand. Thus, a two-eyed hub can be secured to the skin without setting down the staple applicator. In a similar manner, two staples can be used in a situation not requiring a catheter, such as for a small wound that would otherwise be closed by suturing.

Figure 17:
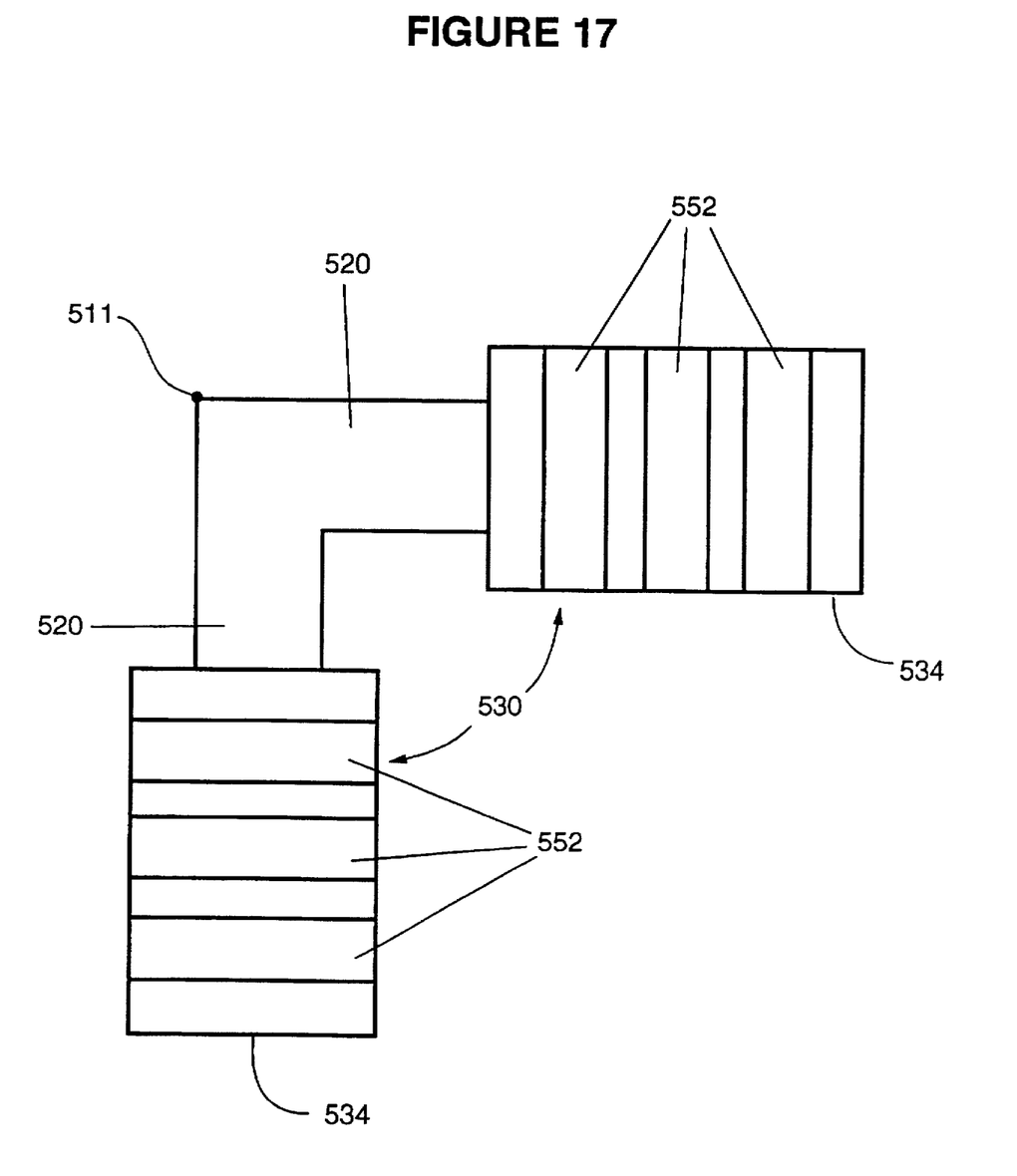
FIG. 17 is another embodiment of the dual applicator assembly.

Another embodiment contemplates three or more staples and applicators. There are a number of ways to join the applicators. One way would be to add additional joining members and assemblies in a manner similar to that in FIG. 12. The preferred arrangement comprises a series of spoke-like joining members emanating from a hub or hub-like point 511 (see FIG. 17) and can be called the L-shaped or partial "ferris wheel" configuration. Two or more spokes 520, like joining member 120 above, and applicator assemblies 530, can be added to the device depicted in FIG. 17. In FIG. 17, ribs 552 correspond to ribs 52 discussed above, and are disposed on the outside face of applicator arms 534.

Figure 12:
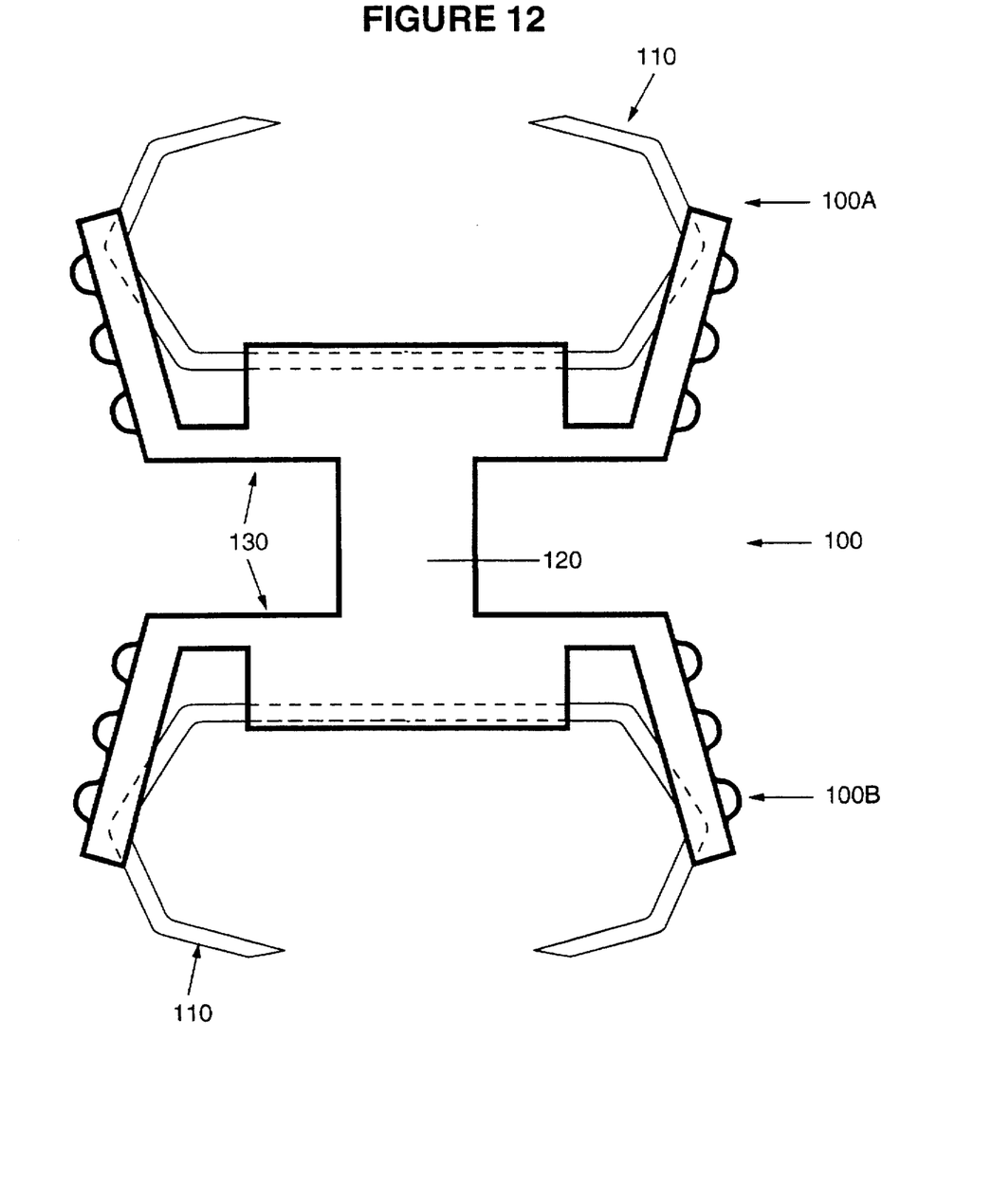
FIG. 12 is an alternate embodiment of the invention, with two applicators joined together.

Another multi-assembly configuration could contain a substantial number of staples mounted inside applicators and arranged in a "centipede" like strip of 4,10,20, or more assemblies. Each assembly could be joined by a short connecting piece, like plastic connector or joining member 120 (FIG. 12). Then the medical care giver could cut off one or two assemblies as necessary.

Numerous other embodiments and uses are contemplated of the present invention, resulting from the simple geometry underlying the staple and staple applicator. As one of ordinary skill in the art can appreciate, grooves 44 and channel 42 function to (1) retain staple 10 in applicator 30 prior to and during the use of the invention, (2) guide the staple downward while it is closing, and (3) stabilize the staple so that it does not rotate around axis A—A through points 25.

Figure 13:
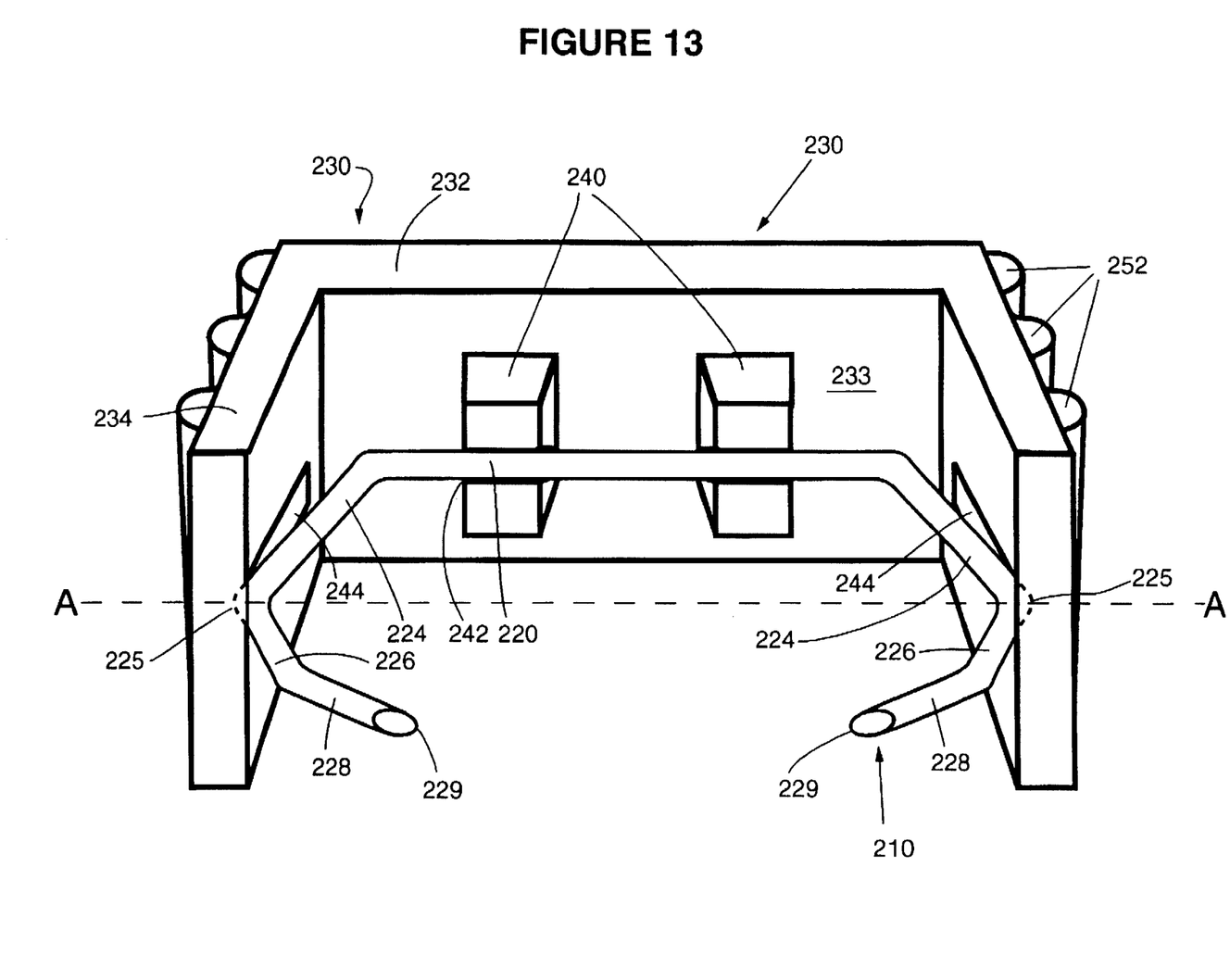
FIG. 13 is a perspective view of the alternate embodiment.

Given the nature of the invention, innumerable additional embodiments can be envisioned. Some examples appear in FIGS. 13–16. In FIG. 13, stabilizing block 40 and channel 42 of FIG. 3 have been replaced by two small stabilizing blocks 240 and two corresponding stabilizing channels 242. Leg segment intersections 225 (FIG. 13), like intersection points 25 (FIG. 3), slide in grooves 244 that retain intersection points 225 and guide the staple in the direction of the skin (not shown). If the intersection points 225 sit shallowly in grooves 244, and the staple is elastic enough, the intersection points may function more like points rather than three dimensional structures. Thus, without stabilizing blocks 240 and channels 242, staple 210 might rotate about axis A—A (FIG. 13).

The device in FIG. 13 could function with only one thin stabilizing block 240 and channel 242, or even simply a clip (not shown) attached to inner backbone face 233 and into which staple crown 220 could fit. An equivalent structure to a stabilizing block and channel (small or large, one or many) would replace block 240 and channel 242 with a slot or hole in applicator backbone 232 into which a pin, hump, or raised portion atop staple crown 220 could be inserted. In other words, any number of male-female attachments could be used to interrelate staple crown 220 and backbone 232 of applicator 230.

Figure 14:
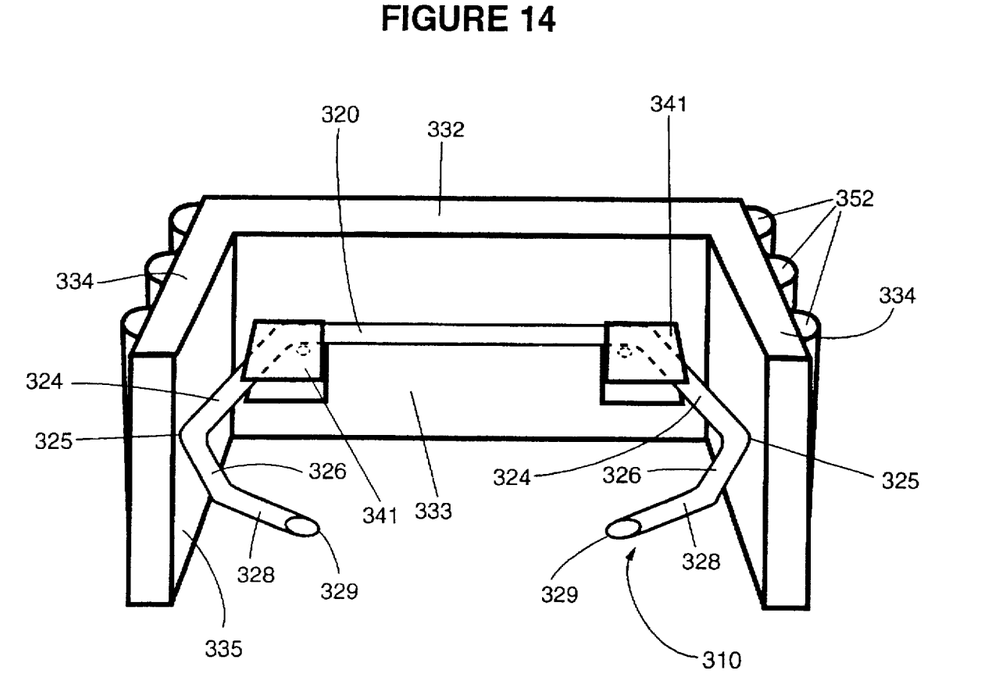
FIG. 14 is a perspective view of another alternate embodiment.
Figure 15:
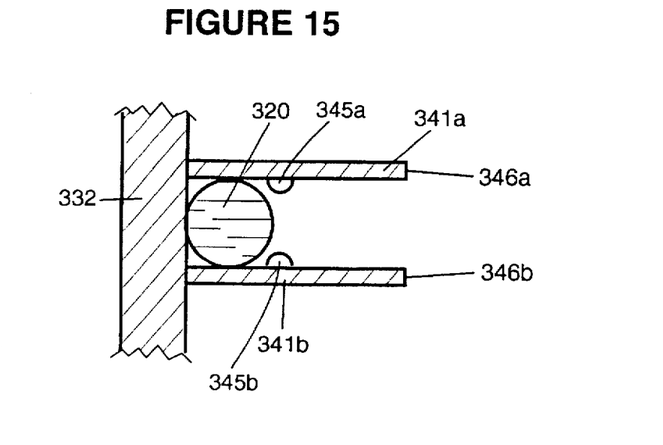
FIG. 15 is a cross section of one of the tabs in FIG. 14.

FIGS. 14 and 15 show still another embodiment of the present invention. Two pairs 341 of tabs 341a and 341b are fastened to inner face 333 of backbone 332. Each tab holds one end of staple crown 320 and an upper portion of leg segment 324. Together, the two tabs 341 both guide staple 310 downward when the applicator arms 334 are squeezed. In addition, the same tabs 341 also stabilize staple 310, preventing it from rotating about an axis through leg segment intersection points 325. The same functions can be accomplished by placing tabs 341 at the top of inner face 335 of applicator arms 334.

Tabs 341 must also retain staple 310 in applicator 330 until the staple is secured to the skin. In the preferred embodiment discussed above (e.g., FIG. 3), staple 10 is fit with slight frictional resistance into grooves 44. FIG. 15 depicts an alternative that can be used with the embodiment of FIG. 14. Two small nubs 345a and 345b retain crown 320 of staple 310, so that a small force must be used to disengage the staple from the tabs by pulling crown 320 through hubs 345a and 345b. An equivalent structure for accomplishing the same result would eliminate hubs 345a,b and instead angle tabs 341a,b so that tab ends 346a,b are separated by a distance slightly less than the diameter of staple 310.

Thus, one of ordinarily skill in the art will understand that a singular structure may provide more than one function. As described above, for example, two sets of tabs 341, as depicted in FIG. 14, could provide the retaining, guiding, and stabilizing functions of the present invention. Grooves 444 in FIG. 16 do likewise.

Figure 16:
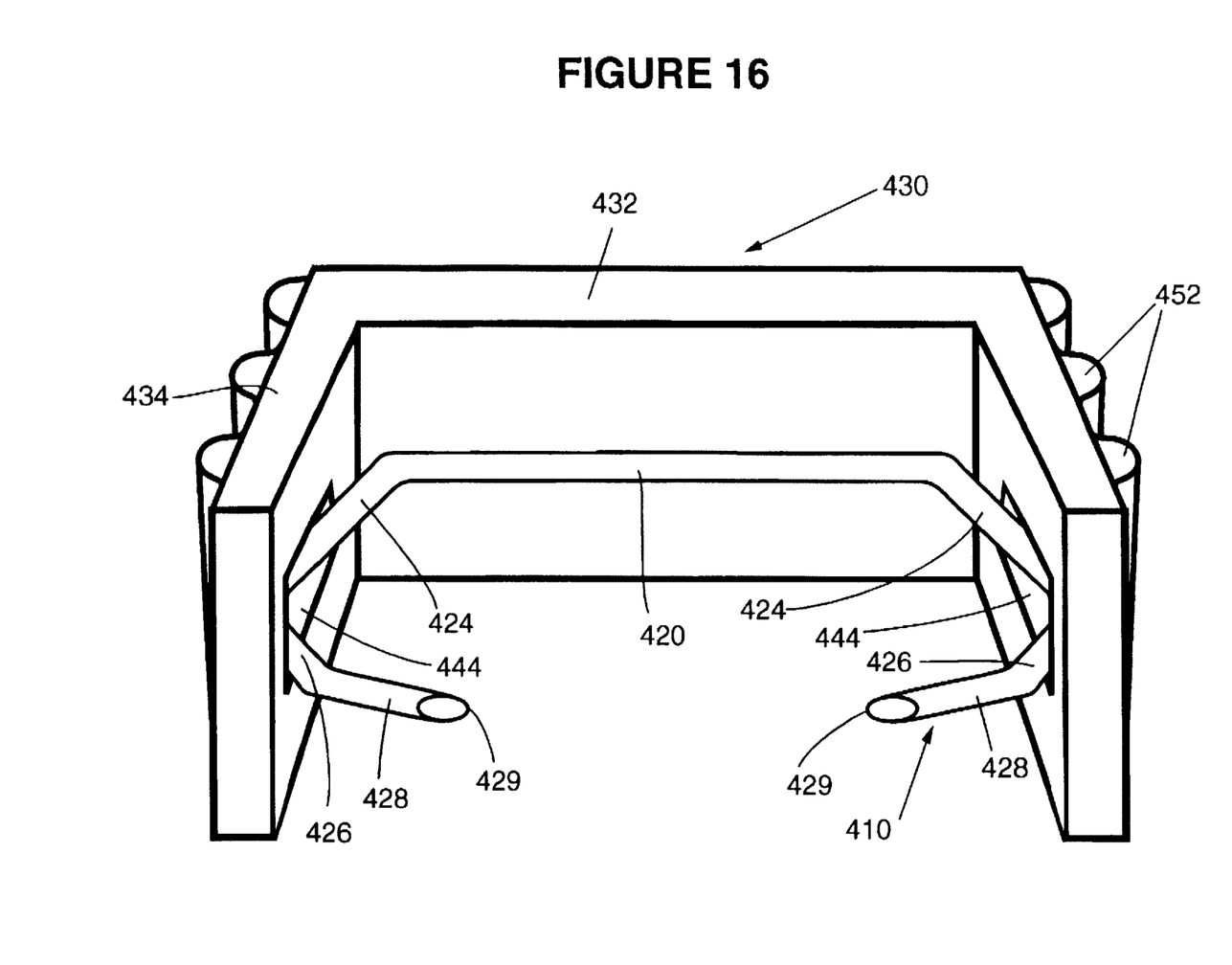
FIG. 16 is yet another embodiment, with deeper grooves.

In keeping with the numerous structures that can comprise the present invention, one of ordinary skill will understand that an improvement of the embodiment in FIG. 14 can be created by adding the guidance grooves 44 depicted in FIG. 3. FIG. 16 alters that configuration by eliminating the tabs, so that grooves 444 accomplish the function of both guiding staple 410 toward its application while retaining the staple in applicator 430 and preventing rotation about intersection points 425 (not shown) where leg segments 424 and 426 meet. Grooves 444 in FIG. 16 differ from grooves 44 in FIG. 3 in that grooves 444 must be deeper than grooves 44, and points 425 must protrude into grooves 444 deeper than do intersection points 25 into grooves 44. Consequently, in FIG. 16, grooves 444 of staple 410 retain the staple so it does not fall out of applicator 430, guide the staple as it changes shape and is secured to the patient, and stabilizes it against rotation. This differs from the configuration in FIG. 3 in that leg segments 24,26 of both legs 22 are inserted into groove 44 shallowly enough that as a practical matter leg segments 24,26 are secured at intersection points 25 more as points than as three dimensional structures.

To describe yet another alternative embodiment, the grooves 444 in FIG. 16 are depicted without curves at the bottom of applicator arm 434. As shown in FIG. 4, the preferred structure terminates grooves 44 with a curved and/or inwardly facing portion 46. In FIG. 16, grooves 444 terminate before the end of applicator arms 434 to ensure that staple 410 does not slide out of groove 444.

The applicator itself can be configured in still other ways, such as by using a different finger grip on the outside face of the applicator arms (e.g., finger cups, polygonal ridges, or simply a rough surface that will not slip) or by shaping the applicator backbone in a different manner. As the preceding discussion demonstrates, there are numerous equivalent structures that can be utilized in the present invention, which one of ordinary skill will understand and appreciate.

Staples of different configuration can be used as long as they function properly with the applicator. They may, for example, include small notches at various positions on the staple to facilitate bending during application, or they may simply be shaped differently than described above.

As noted above, it is contemplated that the present invention could be used in a non-catheter situation for small wounds that require only a few staples, although at some point it becomes more efficient to use a traditional stapler if the wound is too large. Conversely, a dual applicator could be used for only one staple. The wasted material would be of minimal cost and would eliminate the need to manufacture and stock two different varieties of the device. In the claimed method of medical stapling, it is also contemplated that the staple and applicator assembly can be created or fabricated in a number of ways, and that an emergency might even require one to manually insert a single staple into a single applicator. Nor should one be able to defeat the intent of this invention by squeezing the applicator with forceps or the like, rather than with one's own fingers. One could, however, include short handles attached to the applicator arms for ease of handling or leverage in squeezing the applicator arms.

Therefore, it will be understood by those of skill in the art that changes may be made to the present invention in its fabrication and configuration, and that the invention may be used differently without departing from its spirit. The invention is defined in the following claims.

What is claimed is:

1. An assembly for applying a single surgical staple, comprising:

a surgical staple configured to have a crown portion with two ends and two legs disposed at each of said ends, said legs terminating at distal ends with piercing points, each of said legs comprising at least two segments disposed angularly to each other; and a flexible, anvilless, digitally manipulable staple applicator with inner and outer faces, said applicator being comprised of a backbone and two arms extending from said backbone and including means for retaining, guiding, and stabilizing said staple, whereby said staple is releasably mounted in said retaining, guiding, and stabilizing means.

2. The invention of claim 1 further comprising means for facilitating the digital manipulation of said applicator, said means being mounted on said applicator arms.

3. The invention of claim 2 wherein said stabilizing means includes a channel.

4. The invention of claim 3 wherein said channel is disposed within a stabilizing block, said block being disposed upon said inner surface of said backbone.

5. The invention of claim 2 wherein said applicator is manufactured of medical grade plastic.

6. The invention of claim 1 further including at least one groove for guiding said staple during application.

7. The invention of claim 6 wherein said groove is configured to provide all of the functions of retaining, guiding, and stabilizing.

8. The invention of claim 1 wherein each of said staple legs is comprised of at least three adjacent leg segments such that at least a portion of two of said adjacent segments of each of said legs is disposed within said guiding means.

9. The invention of claim 1 wherein said retaining means is located on at least a portion of one of said applicator arms.

10. The invention of claim 9 wherein said retaining, guiding, and stabilizing means comprises at least a pair of tabs mounted on said inner face of said applicator.

11. The invention of claim 1 wherein said retaining and guiding means comprise a groove disposed on said inner face of each of said applicator arms.

12. A dual applicator for holding two surgical staples, each of said staples having a crown portion and two legs, said dual applicator comprising:

two anvilless, digitally manipulable staple applicators with inner and outer faces, each of said applicators being comprised of a backbone and two arm portions extending from said backbone, each of said applicators including means for retaining, guiding, and stabilizing one of said staples, in which said one staple is releasably mounted; and, whereby said dual applicator is formed by joining said two applicators.

13. The invention of claim 12 wherein said applicators are arranged in a ferris wheel configuration.

14. The invention of claim 12, further comprising at least one additional of said surgical staples and one additional of said applicators.

15. A method of applying a surgical staple to a patient, comprising the steps of:

furnishing an assembly of a single, pre-formed, deformable surgical staple and a digitally manipulable, anvilless staple applicator configured to hold said staple, said staple applicator having a backbone and two associated arm portions, said applicator further having inner and outer faces, and said staple having legs terminating at distal ends with piercing points, said applicator including means for retaining, guiding, and stabilizing said staple, whereby said staple is releasably mounted in at least one of said retaining, guiding, and stabilizing means;

holding said assembly in the fingers of one hand;

placing said staple piercing points adjacent to a location on said skin where said staple is to be applied;

squeezing said applicator arms to apply force directly to said staple, wherein said staple will bend in response to said force applied by said arms; and releasing said applicator arms and disengaging said applicator from said staple.

16. The method of claim 15, wherein said staple and applicator assembly comprises at least two applicators and two associated staples, and wherein all steps of claim 11 are performed in applying a first of said two staples, further comprising:

the step of manually repositioning said applicator for application of said second staple; and, repeating said steps of claim 11 for application of said second staple, beginning with said step of holding said assembly in the fingers of one hand.

17. The method of claim 15, further comprising the additional steps of:

tenting said skin; and, holding a catheter hub in close proximity with said tented skin such that at least one of said staple points can pass through said hub, securing said hub to said skin said additional steps of tenting the skin and holding the catheter hub being performed proximate the steps of holding and placing in claim 11.

18. The method of claim 15, wherein said guiding, retaining, and stabilizing means comprises grooves disposed on said inside face of said applicator arms and at least one of a stabilizing channel, tab, and clip disposed on said inside face of said applicator.

19. The invention of claim 1 wherein said stabilizing means comprises at least one of a stabilizing channel, a clip, and tabs.

* * * * *